United States Patent [19]

Petrow et al.

[11] 4,396,615

[45] Aug. 2, 1983

[54] METHOD OF TREATING ANDROGEN-RELATED DISORDERS

[75] Inventors: Vladimir Petrow, Chapel Hill; Leon Lack, Durham, both of N.C.

[73] Assignee: Duke University, Durham, N.C.

[21] Appl. No.: 278,373

[22] Filed: Jun. 24, 1981

[51] Int. Cl.$^3$ .............................................. A61K 31/56
[52] U.S. Cl. .................................... 424/242; 260/397.3
[58] Field of Search ......................... 424/238, 243, 242

[56] References Cited

U.S. PATENT DOCUMENTS 4,055,641 10/1977 Benson et al. ...................... 424/243

OTHER PUBLICATIONS

Chemical Abstracts, vol. 67, (1967), Para. 91,029(p).

Primary Examiner—Elbert L. Roberts
Attorney, Agent, or Firm—Oblon, Fisher, Spivak, McClelland & Maier

[57] ABSTRACT

A method of treating androgen-related disorders in an animal which comprises administering to the animal dihydrotestosterone level decreasing amounts of a compound of formula (I):

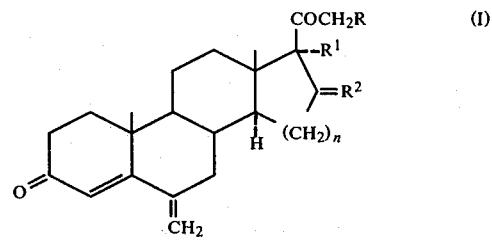

wherein R is H or F; $R^1$ is selected from the group consisting of —H; straight or branched chain lower alkyl; hydroxyl; —OCOR$^3$; and O—(C$_1$–C$_6$ alkyl); wherein $R^3$ is —H, C$_1$–C$_{10}$ straight or branched chain alkyl group, phenyl, phenyl alkylene having straight or branched chain C$_1$–C$_6$ alkylene, C$_5$–C$_{10}$ cycloalkyl or C$_6$–C$_{10}$ cycloalkyl alkylene; $R^2$ is H$_2$, methylene, ethylidene, α-CH$_3$(H), β-CH$_3$(H), α-(OH)(H) or the acetonide derived from the 16α,17α-dihydroxy derivative, and n is 1 or 2.

8 Claims, 2 Drawing Figures

METHOD OF TREATING ANDROGEN-RELATED DISORDERS

BACKGROUND OF THE INVENTION

The invention described herein was made in the course of work under a grant or award from the Department of Health and Human Services.

1. Field of the Invention

This invention relates to methods of treating androgen-related disorders and pharmaceutical compositions useful for such treatment.

2. Description of the Prior Art

Considerable experimental evidence exists supporting the conclusion that the 5α-reduced metabolite of testosterone (II), 5α-dihydrotestosterone (III)

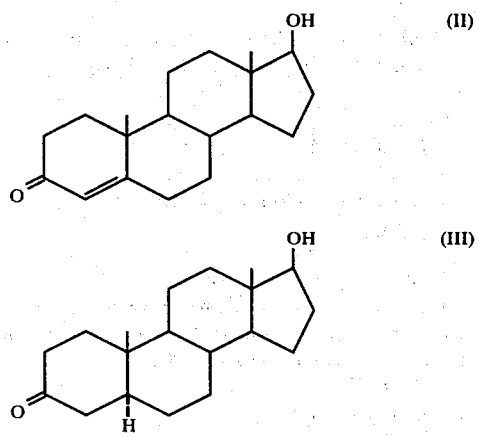

Ps is the active form of the androgenic hormone responsible for eliciting somatic androgenic effects, and that testosterone (II), is, de facto, a prohormone [cf. for example, Gloyna, R. E. and Wilson, J. D., J. Clin. Endocrinol. 29:970(1969); Mainwaring, W. I. P., Mangan, F. R., Wilce, P. A. and Melroy, E. G. P., Advances in Experimental Medicine and Biology, 36:197(1973); Liao, S., International Review of Cytology, 41:87(1975)]. It is consequently generally accepted that androgen-related disorders stem from excessive production of dihydrotestosterone in the body. Such androgen-related disorders include

- acne
- oily skin
- seborrhea
- androgenic alopecia
- hirsutism
- androgen-dependent prostatic cancer
- prostatic hypertrophy and
- virilism.

It follows that treatment, or palliative treatment in the case of hormone-dependent carcinoma, of these disorders may be effected by inhibiting the conversion of (II) into (III).

The conversion of testosterone (II) into dihydrotestosterone (III) in the body is effected by the NADPH-dependent enzyme 5α-reductase. Treatment of androgen-related disorders may thus be achieved by inhibiting the enzyme 5α-reductase. This fact is well-documented in the literature (cf. for example, U.S. Pat. No. 3,917,829; U.S. Pat. No. 4,088,760). Progesterone appears to be a preferred substrate for the enzyme (cf. for example, Voight, W., Fernandez, E. P. and Hsia, S. L., J. Biol. Chem. 245:5594(1970)), and is well-known to be a reversible and competitive inhibitor of the enzyme. It is therefore not surprising that progesterone has been used to counteract excessive dihydrotestosterone production. Thus topical administration of a 0.5% solution of progesterone in aqueous ethanol caused an important decrease in sebum secretion in 45/53 males with acne [cf. Vermorken, A. J. M. and Jouben, J. J. G., Drug. Intel, Clin. Pharm., 12:151–157(1978)]. A pro-drug form of progesterone is claimed in Bodor, N. S. and Sloan, K. B., U.S. Pat. No. 4,213,978/1980, as useful in the treatment of acne and seborrhea. Progesterone strongly inhibits the enzyme in cell-culture preparations of human prostate thereby inhibiting growth of the tissue [Sandberg, A., U.I.C.C. Technical Report Series 48:165(1979), see also Massa, R. and Martini, L., Gynec. Invest. 2:253(1971/2)]. Inhibition of the conversion of testosterone to dihydrotestosterone by progesterone in preparations of human benign prostatic hypertrophic tissue has been reported by Tau, S. Y., Antonpillai, I. and Pearson Murphy, B. E. [J. Clin. Endocrinol. Metab. 39:936(1974)]. However, the value of progesterone as an inhibitor of 5α-reductase, and hence as a therapeutic agent in the treatment of androgen-related disorders, is limited by the following:

(i) It is a competitive (reversible) inhibitor of the enzyme. It is now widely recognized that an irreversible inhibitor offers a distinct advantage over a reversible inhibitor in that it can induce prolonged inactivation of the enzyme and combat the effects of physiological dilution [cf. for example, Shaw, E., in Enzyme Inhibitors as Drugs, Ed. Sandler, M., MacMillan Press, p. 25, 1980];

(ii) It undergoes metabolism in the body to androstenedione and other androgenic metabolites and is thus unsuitable for systemic administration.

A need therefore exists for progesterone derivatives which are irreversible inhibitors of the enzyme 5α-reductase.

SUMMARY OF THE INVENTION

It is therefore an object of the invention to provide a method of treating androgen-related disorders.

It is another object of the invention to provide a method as hereinbefore, which utilizes an irreversible inhibitor of the enzyme testosterone-5α-reductase.

Yet another object of the invention is to provide pharmaceutical compositions for the treatment of androgen-related disorders.

These and other objects of the invention as will hereinafter become more readily apparent have been attained by providing:

A method for the treatment of androgen-related disorders in an animal which comprises administering to said animal a compound of the formula (I)

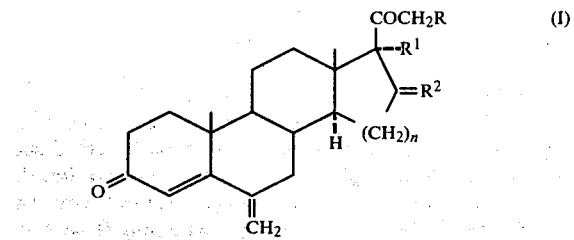

wherein
R is H or F

R' is selected from the group consisting of —H; straight or branched chain lower alkyl; hydroxyl; —OCOR³ and O—(C₁–C₆ alkyl); wherein R³ is —H, C₁–C₁₀ straight or branched chain alkyl group, phenyl, phenyl alkylene having straight or branched chain C₁–C₆ alkylene, C₅–C₁₀ cycloalkyl or C₆–C₁₀ cycloalkylalkylene;

R² is H₂, methylene, ethylidene, α-CH₃(H), β-CH₃(H), α(OH)H, or the acetonide derived from the 16α,17α-dihydroxy derivative, and n is 1 or 2.

This invention also relates to pharmaceutical preparations suitable for treating androgen-related disorders.

DESCRIPTION OF THE PREFERRED EMBODIMENTS

Figure 1:
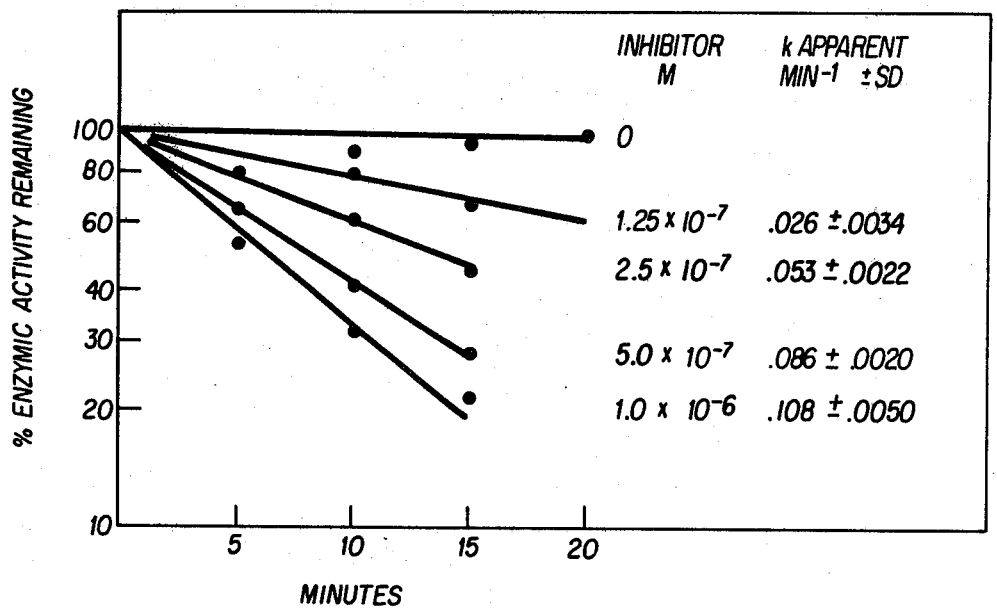
FIG. 1 shows the time course of inactivation of 5α-reductase following incubation of the enzyme with NADPH and 17α-acetoxy-6-methyleneprogesterone; see Example 2.

As used herein the term androgen-related disorder is intended to mean any disease or condition resulting from overproduction of dihydrotestosterone in the body including acne, oily skin, seborrhea, androgenic alopecia, hirsutism, virilism, androgen-dependent prostatic carcinoma and benign prostatic hypertrophy.

For a more detailed description of these conditions, see for example Harrison's Principles of Internal Medicine, 9th Edition, Mc-Graw Hill, 1980, Volume 1, pp. 227–229 (hirsutism, virilism), volume 1, pages 242–243 (acne), volume 2, pages 1771–1772 (cancer of the prostate), which pages are herein incorporated by reference.

It is the object of this invention to provide pharmaceutical preparations of the steroids of formula (I) which can be administered to a patient suffering from an androgen-related disorder; this novel method of treatment offers considerable advantages over prior art, for example over estrogen therapy, in that it is free from deleterious side effects such as estrogenization.

The compounds used in the invention have the formula (I):

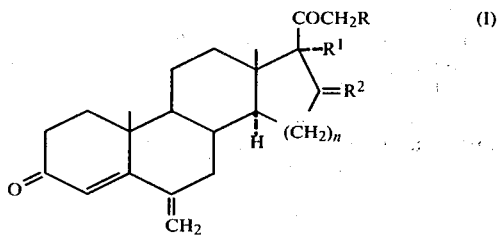

wherein
R is H or F;
R' is H; lower alkyl containing from 1 to 6 carbon atoms, which may be straight or branched chain such as for example methyl, ethyl, n-propyl, butyl, isobutyl and the like; hydroxyl; OCOR³ wherein R³ may be H, an alkyl moiety containing from 1 to 10 carbon atoms and may be straight or branched chain, such as for example methyl, ethyl, n-propyl, isopropyl, n-butyl, sec-butyl, tert-butyl, n-pentyl, neopentyl, pivalyl, hexyl, heptyl, octyl and the like; phenyl; phenylalkyl (Ph-alkyl-) wherein the alkyl moiety (which may also be referred to as an alkylene moiety) has from 1 to 6 carbon atoms and can be straight or branched chain; cycloalkyl wherein the cycloalkyl moiety has from 5 to 10 carbon atoms such as cyclopentyl-, cyclohexyl-, cycloheptyl, cyclooctyl- and their alkylene derivatives containing from 6 to 16 carbon atoms such as cyclopentylmethylene C₅H₉CH₂—; O-lower alkyl, wherein the alkyl group has from 1 to 6 carbon atoms and may be straight or branched chain such for example as methyl-, ethyl-, propyl-, iso-propyl-, iso-pentyl, butyl, isobutyl, pentyl;

R² is H₂, methylene, ethylidene, α-Me(H), β-Me(H), α-(OH)H, and the acetonide derived from the 16α,17α-dihydroxy derivative;

n is 1 or 2.

Preferred embodiments of this invention include the following derivatives of 6-Methyleneprogesterone:

17α-acetoxy:
17α-acetoxy-D-homo-
17α-acetoxy-21-fluoro-
17α-acetoxy-21-fluoro-D-homo
17α-caproyloxy-
17α-caproyloxy-D-homo
17α-caproyloxy-21-fluoro-
17α-caproyloxy-21-fluoro-D-homo; the 16α-methyl-, 16β-methyl- and 16-methylene and ethylidene derivatives of the above (when n=1),
17α-methyl-
17α-methyl-D-homo-
17α-methyl-21-fluoro-
17α-methyl-21-fluoro-D-homo-; the 17α-ethyl analogues of the above and their 16α- and 16β-methyl-derivatives (when n=1),
17α-methoxy-
17α-methoxy-D-homo-
17α-methoxy-21-fluoro-
17α-methoxy-21-fluoro-D-homo-
17α-ethoxy-
17α-ethoxy-D-homo-
17α-ethoxy-21-fluoro-
17α-ethoxy-21-fluoro-D-homo-; the 16α-methyl, 16β-methyl and 16-methylene and ethylidene derivatives of the above (when n=1),
acetonide from 16α,17α-dihydroxy derivative (when n=1)
acetonide from the 21-fluoro-16α,17α-dihydroxy derivative (when n=1) and the D-homo analogs of the above
6-methylene progesterone and its
21-fluoro-
16α-methyl-
21-fluoro-16α-methyl-
16β-methyl
21-fluoro-16β-methyl and D-homo analogues of the above.

Most of the compounds claimed in this invention are already known in the art. Those that are not known can be readily prepared from the known and appropriate progesterone derivatives by the Vilsmeier or analogous processes as reported, for example, in the following publications:

D. Burn et al, Tetrahedron 20:597(1964).
F. Schneider et al, Helv. Chim. Acta 56:2396(1973).
M. Müller et al, Helv, Chim. Acta 63:1857(1980).
D. Burn et al, Tetrahedron 21:569(1965).
V. Petrow, Chemical Reviews 70:713(1970).
K. Bruckner et al, U.S. Pat. No. 3,449,495 (1969).
D. N. Kirk and V. Petrow, U.S. Pat. No. 3,112,305.
F. B. Colton, U.S. Pat. No. 2,980,711.
The Upjohn Co. B.P. 1,271,207.

These publications are herein incorporated by reference.

The compounds employed in the present invention can be administered in various manners to achieve the desired dihydrotestosterone-decreasing effect. The compounds can be administered alone or in the form of pharmaceutical preparations to the patient being treated orally, parenterally or topically.

Topical administration is preferred for acne and seborrhea. The amount of compound administered will vary with the severity of the condition being treated. For oral and parenteral administration the daily dose will generally be from 0.1 to 50 mg/Kg and preferably from 1 to 30 mg/Kg. Unit dosages for oral or parenteral administration may contain, for example, from 5 to 500 mg of the active ingredient.

For topical administration effective amounts of the compounds of general formula (I) on a percent basis may vary from 0.001% to 5% and preferably from 0.005% to 1%. For topical administration the formulated active ingredient, that is a compound of general formula I, can be applied directly to the site requiring treatment or can be applied to the oral or nasal mucosa. Applicator sticks carrying the formulation may be employed in administering the compounds. The topical formulation can be, for example, in the form of a solution, suspension, emulsion, gel or cream of either the oil-in-water or water-in-oil type, ointment, paste, jelly, paint or powder. Suitable bases for the topical preparation may be of any conventional type such as oleaginous bases, for example, olive oil, cottonseed oil, petrolatum, white petrolatum, mineral oils, silicones, such as dimethylpolysiloxane, or methylphenylpolysiloxane, lanolins, polyethyleneglycol, glyceryl monostearate, methylcellulose and hydroxymethylcellulose. The topical formulation may contain pharmaceutically acceptable surfactants, wetting agents, dispersing agents, emulsifiers, penetrants, emollients, detergents, hardeners, preservatives, fillers, antioxidants, perfumes, cooling agents, such as menthol, soothing agents, such as camphor, or coloring agents, such as zinc oxide. Aerosol preparations of a solution, suspension or emulsion containing the active ingredient in the form of a finely ground powder can also be employed for topical administration. The aerosol may be packaged in a pressurized aerosol container together with a gaseous or liquified propellant, for example, dichlorofluoromethane, dichlorodifluoromethane with dichlorodifluoroethane, carbon dioxide, nitrogen, or propane with the usual adjuvant such as cosolvent and wetting agents as may be necessary or desirable. The compounds may also be administered in a nonpressurized form such as in a nebulizer or atomizer.

For oral administration the compounds can be formulated into solid or liquid preparations, such as capsules, pills, tablets, troches, powders, solutions, suspensions or emulsions. The compounds can be applied in the form of an aerosol containing finely divided particles of the active ingredient. The solid unit dosage forms can be a capsule which can be of the ordinary gelatin type containing a compound of general formula I and a carrier, for example, lubricants and inert filler such as lactose, sucrose, and corn starch. In another embodiment the compounds of the general formula I can be tableted with conventional tablet bases such as lactose, sucrose and corn starch in combination with binders such as acacia, corn starch or gelatin, disintegrating agents such as potato starch or aliginic acids and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such a water-in-oil with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanols and glycols, such as propylene glycol or polyethylene glycol are preferred liquid cariers, particularly for injectable solutions.

The compounds can be administered in the form of a depot injection or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones. For example, Silastic, silicone rubber manufactured by the Dow-Corning Corporation.

The compounds of general Formula I in treating acne and oily skin conditions may be used in combination with other anti-acne preparations, antiseptics, anti-infective agents, keratolytic agents, for example, benzoic acid, resorcinol or salicylic acid, and comedolytic agents, such as, retinoic acid or agents having a retinoic acidlike action, corticoids or other antiinflammatory agents, thioglycolates, ethyl lactate or benzoyl peroxide.

In using the products of this invention, topical administration is preferred for acne and seborrhea. The remaining conditions are preferably treated by sytemic administration. In treating benign prostatic hypertrophy and prostatic carcinoma, improved results are obtained by administering the products of the invention concurrently with megestrol acetate, chlormadinone acetate, medrogestone or cyproterone acetate at therapeutic dose levels.

Having now generally described this invention, the same will be better understood by reference to certain specific examples which are included herein for purposes of illustration only, and are not intended to be limiting unless otherwise specified.

BIOLOGICAL RESULTS

Example 1

The compounds of the present invention represent an important advance over progesterone and derivatives thereof since they are irreversible inhibitors of the enzyme 5α-reductase. Employing the assay of R. J. Moore and J. D. Wilson [Methods in Enzymology, Vol. XXXVI, Academic Press, N.Y., Ed. W. O'Malley and G. Hardman, p. 466-474(1975)], it is found that 6-methyleneprogesterone and 17α-acetoxy-6-methyleneprogesterone, for example are equipotent with progesterone as inhibitors of the enzyme. On preincubating the enzyme with 17α-acetoxy-6-methyleneprogesterone and NADPH, diluting tenfold and assaying for 5α-reductase activity, it is surprisingly found, however, that 75% of the enzyme activity is lost. Similar preincubation of the enzyme with progesterone, in striking contrast, does not result in enzyme inactivation. These results are tabulated below, in Tables 1 and 2.

TABLE 1

Effect of Preincubation of Enzyme with 17-Acetoxy-6-methylene-4-pregnen-3,20-dione and NADPH on 5α-Reductase Activity

| Preincubation conditions Time: 15 min | | Enzymic Assay conditions Time: 45 min | | | Picomol Testosterone reduced/mg protein |
|---|---|---|---|---|---|
| Inhibitor | NADPH | Inhibitor | Testosterone | NADPH | in 45 min + SEM |
| M | | M | | | |
| A $5 \times 10^{-7}$ | $6 \times 10^{-5}$ | $5 \times 10^{-8}$ | $5 \times 10^{-8}$ | $5 \times 10^{-4}$ | $0.71 \pm 0.018$n = 6 |
| B 0 | $6 \times 10^{-5}$ | $5 \times 10^{-8}$ | $5 \times 10^{-8}$ | $5 \times 10^{-4}$ | $3.0 \pm 0.26$n = 6 |
| C 0 | 0 | $5 \times 10^{-8}$ | $5 \times 10^{-8}$ | $5 \times 10^{-4}$ | $2.83 \pm 0.09$n = 6 |
| D $5 \times 10^{-7}$ | 0 | $5 \times 10^{-8}$ | $5 \times 10^{-8}$ | $5 \times 10^{-4}$ | $2.63 \pm 0.18$n = 6 |
| E No preincubation | | 0 | $5 \times 10^{-8}$ | $5 \times 10^{-4}$ | $4.36 \pm 0.24$n = 4 |
| F No preincubation | | $5 \times 10^{-8}$ | $5 \times 10^{-8}$ | $5 \times 10^{-4}$ | $3.14 \pm 0.20$n = 4 | n = number of experiments

TABLE 2

Effect of Preincubation of Enzyme with Progesterone and NADPH on 5α-Reductase Activity

| | Preincubation conditions Time: 15 min | | Conditions during enzymic assay 45 min | | | Picomol Testosterone Reduced/mg protein in 45 min |
|---|---|---|---|---|---|---|
| | Progesterone | NADPH | Progesterone | NADPH | Testosterone | |
| 1 | 0 | $6 \times 10^{-5}$ | $5 \times 10^{-8}$ | $5 \times 10^{-4}$ | $5 \times 10^{-8}$ | 3.91 |
| | 0 | $6 \times 10^{-5}$ | $5 \times 10^{-8}$ | $5 \times 10^{-4}$ | $5 \times 10^{-8}$ | 3.41 |
| 2 | $5 \times 10^{-7}$ | $6 \times 10^{-5}$ | $5 \times 10^{-8}$ | $5 \times 10^{-4}$ | $5 \times 10^{-8}$ | 3.91 |
| | $5 \times 10^{-7}$ | $6 \times 10^{-5}$ | $5 \times 10^{-8}$ | $5 \times 10^{-4}$ | $5 \times 10^{-8}$ | 3.79 |
| 3 | No preincubation | | 0 | $5 \times 10^{-4}$ | $5 \times 10^{-8}$ | 5.80 |
| | No preincubation | | 0 | $5 \times 10^{-4}$ | $5 \times 10^{-8}$ | 5.42 |
| 4 | No preincubation | | $5 \times 10^{-8}$ | $5 \times 10^{-4}$ | $5 \times 10^{-8}$ | 3.66 |
| | No preincubation | | $5 \times 10^{-8}$ | $5 \times 10^{-4}$ | $5 \times 10^{-8}$ | 3.54 |

These observations reveal that 17α-acetoxy-6-methyleneprogesterone, in striking contrast to progesterone, combines with the enzyme in the presence of the co-factor NADPH in an irreversible manner, whilst progesterone inactivation of the enzyme is competitive and reversible.

Example 2

The time course of inactivation of 5α-reductase following incubation of the enzyme with NADPH and 17α-acetoxy-6-methyleneprogesterone is shown in FIG. 1.

Figure 2:
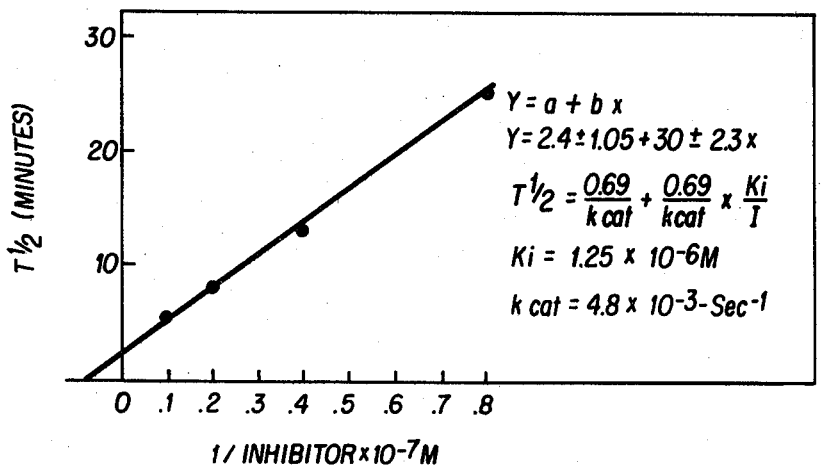
FIG. 2 demonstrates that the inactivation of the enzyme 5α-reductase follows saturation kinetics, since the plot of the rate constants (as T½'s) versus 1/[Inhibitor] is linear; see Example 2.

This time course of inactivation of the enzyme can be seen to follow pseudo first-order kinetics, which is in accord with the postulate that the inhibition invoked by such preincubation exposure is irreversible. When these rate constants are plotted (as the $t_{\frac{1}{2}}$'s) against the reciprocal of the inhibitor concentrations, a straight line is obtained with a positive intercept on the y-axis, indicating a saturation phenomenon (FIG. 2). These data are in accord with the conclusion that the interaction of the inhibitor with the enzyme shows two phases. The first is a reversible combination of the enzyme and inhibitor with a Ki of $1.25 \times 10^{-6}$M. The enzyme-inhibitor complex then undergoes irreversible combination rendering the enzyme inactive. The rate constant for this step ($k_{cat}$) is $4.8 \times 10^{-3}$ sec$^{-1}$.

Formulations

Following are illustrative topical pharmaceutical formulations which may be employed in practicing the present invention:

Example 3

| Solution | |
|---|---|
| 17α-Acetoxy-6-methyleneprogesterone | 0.85 g |
| Alcohol | 78.9 ml |
| Isopropyl Myristate | 5.0 g |
| Polyethylene Glycol 400 | 10.0 g |
| Purified Water qs ad | 100. ml |

Combine the alcohol, isopropyl myristate and polyethylene glycol 400 and dissolve the drug substance therein. Add sufficient purified water to give 100 ml.

Example 4

| A Gel | |
|---|---|
| 17α-Acetoxy-6-methyleneprogesterone | 0.85 g |
| Alcohol | 78.9 ml |
| Isopropyl Myristate | 5.0 g |
| Polyethylene Glycol 400 | 10.0 g |
| Carbopol 940 (Carboxypolymethylene) | 0.75 g |
| Triethylamine | . qs |
| Purified Water qs ad | 85. g |

Disperse the Carbopol 940 in the isopropyl myristate. To 38 ml of alcohol add 7 ml of purified water and the polyethylene glycol 400 and mix. Combine the two phases and mix until well dispersed. Add sufficient triethylamine to give a neutral pH. Dissolve the drug substance in the balance of the alcohol and mix well into the batch. Add and mix sufficiently purified water to provide 85 g of finished product.

Example 5

| Applicator Stick | |
|---|---|
| 17α-Acetoxy-6-methyleneprogesterone | 0.85 g |
| Absolute Alcohol | 75. ml |
| Polyethylene Glycol 400 | 10.0 g |
| Isopropyl Myristate | 5.0 g |
| Stearic Acid | 4.3 g |
| Sodium Hydroxide | 0.55 g |
| Purified Water qs ad | 85. g |

Combine the absolute alcohol, polyethylene glycol 400 and isopropyl myristate and dissolve the drug substance therein. Add the stearic acid and heat the mixture to about 65° C. Dissolve the sodium hydroxide in a small amount of water, add and mix. Add sufficient water to provide 85 g of finished product. Pour into suitable molds and allow to solidify.

Example 6

| Aerosol Foam | |
|---|---|
| 17α-Acetoxy-6-methyleneprogesterone | 1.0 g |
| Propylene Glycol | 96.0 g |
| Emulsifying Wax NF XIV | 3.0 g |
| Dichlorodifluoromethane:cryfluorane (20:80) | 6.9 g |

Dissolve the drug substance in the propylene glycol. Add the emulsifying wax and heat to approximately 70° C. Stir while cooling to room temperature. Charge a suitable aerosol unit with this concentrate and 6.9 g of dichlorodifluoromethane:cryofluorane (20:80).

Example 7

| Topical Cream, Vanishing, o/w | |
|---|---|
| 17α-Acetoxy-6-methyleneprogesterone | 1. |
| Stearic Acid | 15. |
| Sorbitan Monostearate | 2. |
| Polyoxyethylene Sorbitan Monostearate | 2.3 |
| Propylene Glycol | 5. |
| Methylparaben | 0.025% |
| Propylparaben | 0.015% |
| Purified Water | qs |

Example 8

| Buccal or Sublingual Tablet | |
|---|---|
| 17α-Acetoxy-6-methyleneprogesterone | 1% |
| Calcium Stearate | 1% |
| Calcium Saccharin | 0.02% |
| Granular Mannitol | qs |

Mix and compress on a suitable tablet machine to a weight of 0.115 g/tablet.

Example 9

| Powder | |
|---|---|
| 17α-Acetoxy-6-methyleneprogesterone, micronized | 1 |
| Silicon dioxide, anhydrous | 0.5 |
| Corn starch, lactose, fine powder aa | qs |

Example 10

| Oleaginous Ointment | |
|---|---|
| 17α-Acetoxy-6-methyleneprogesterone | 1 |
| White wax | 5 |
| White petrolatum qs | 100 |

Example 11

| Absorption Ointment Base | |
|---|---|
| 17α-Acetoxy-6-methyleneprogesterone | 1 |
| Cholesterol | 3 |
| Stearyl alcohol | 3 |
| White wax | 8 |
| White petrolatum qs | 100 |

Example 12

| Water Soluble Ointment Base | |
|---|---|
| 17α-Acetoxy-6-methyleneprogesterone | 1 |
| Polyethylene glycol 4000 | 40 |
| Polyethylene glycol 400 qs | 100 |

Example 13

| Paste | |
|---|---|
| 17α-Acetoxy-6-methyleneprogesterone | 1 |
| Starch | 25 |
| Zinc oxide | 25 |
| White petrolatum qs | 100 |

Example 14

| Aerosol Foam | |
|---|---|
| 17α-Acetoxy-6-methyleneprogesterone | 1 |
| Emulsifying wax | 3 |
| Stearic acid | 1 |
| Stearyl alcohol | 1 |
| Diglycol stearate | 2 |
| Propylene glycol | 92 |

The following are illustrative pharmaceutical formulations suitable for oral or parenteral administration which may be employed in practicing the present invention:

Example 15

| Tablet | For 15,000 |
|---|---|
| 17α-Acetoxy-6-methyleneprogesterone | 75. g |
| Lactose | 1.216 Kg |
| Corn Starch | 0.3 Kg |

Mix the active ingredient, the lactose and corn starch uniformly. Granulate with 10% starch paste. Dry to a moisture content of about 2.5%. Screen through a No. 12 mesh screen. Add and mix the following:

| | |
|---|---|
| Magnesium Stearate | 0.015 Kg |
| Corn Starch qs ad | 1.725 Kg |

Compress on a suitable tablet machine to a weight to 0.115 g/tablet.

Example 16

| Soft Gelatin Capsule | |
|---|---|
| 17α-Acetoxy-6-methyleneprogesterone | 0.25 Kg |
| Polysorbate 80 | 0.25 Kg |
| Corn Oil qs ad | 25.0 Kg |

Mix and fill into 50,000 soft gelatin capsules.

Example 17

| IM Depot Injection | |
|---|---|
| Each 1 ml contains the following: | |
| 17α-Acetoxy-6-methyleneprogesterone | 5.0 mg |
| Anhydrous Chlorobutanol | 5.0 mg |
| Aluminum Monostearate | 50.0 mg |
| Peanut Oil qs ad | 1.0 ml |

Dissolve or disperse the ingredients in the peanut oil.

Example 18

| Depot-Implant | |
|---|---|
| 17α-Acetoxy-6-methyleneprogesterone | 5. mg |
| Dimethylsiloxane | 240. mg |
| Catalyst qs | |

Disperse the drug substance in the fluid dimethylsiloxane. Add the catalyst and cast into a suitable monolytic structure.

Alternatively, the drug substance may be enclosed by a precast polydimethylsiloxane envelope.

Alternatively, the drug substance may be dispersed in a suitable amount of hydroxyethyl acrylate subsequently polymerized and cross-linked by the addition of ethylenedimethacrylate, and an oxidizing agent, to yield a 3-dimensional ethylene glycomethacrylate mouldable gel (Hydron).

Example 19

| IM Injections | | |
|---|---|---|
| A. | Oil Type: | |
| | 17α-Acetoxy-6-methyleneprogesterone | 25. mg |
| | BHA, BHT aa | 0.01% w/v |
| | Peanut Oil or Sesame Oil qs | 1.0 ml |
| B. | Suspension Type: | |
| | 17α-Acetoxy-6-methyleneprogesterone | 25. mg |
| | Sodium Carboxymethylcellulose | 0.5% w/v |
| | Sodium Bisulfite | 0.02% w/v |
| | Water for Injection, qs | 1.0 ml |

Example 20

| Buccal or Sublingual Tablet | |
|---|---|
| 17α-Acetoxy-6-methyleneprogesterone | 1% |
| Calcium Stearate | 1% |
| Calcium Saccharin | 0.02% |
| Granular Mannitol | qs |

Mix and compress on a suitable tablet machine to a weight of 0.115 g/tablet.

The following formulations are illustrative of pharmaceutical preparations for topical application comprising a compound of general Formula I in combination with a keratolytic agent.

Example 21

| Aerosol Foam | % w/w |
|---|---|
| 17α-Acetoxy-6-methyleneprogesterone | 1 |
| Resorcinol monoacetate | 1 |
| Emulsifying wax NF | 3 |
| Stearic acid | 1 |
| Stearyl alcohol | 1 |
| Diglycol stearate | 2 |
| Propylene glycol | 91 |

Dissolve the drug substance in the propylene glycol. Add the emulsifying wax and heat to about 70° C. Stir while cooling to room temperature. Charge a suitable aerosol unit with the concentrate and 6.9 g of dichlorodifluoromethane:cryfluorane (20:80).

Example 22

| A Gel | |
|---|---|
| 17α-Acetoxy-6-methyleneprogesterone | 0.85 g |
| Resorcinol | 0.85 g |
| Alcohol | 78.9 ml |
| Isopropyl myristate | 5.0 g |
| Polyethylene glycol 400 | 10.0 g |
| Carbopol 940 (carboxypolymethylene) | 0.75 g |
| Triethylamine | qs |
| Purified water qs ad | |

Disperse the Carbopol 940 in the isopropyl myristate. To 38 ml of alcohol add 7 ml of purified water and the polyethylene glycol 400 and mix. Combine the two phases and mix until well dispersed. Add sufficient triethylamine to give a neutral pH. Dissolve the drug substance and the resorcinol in the balance of the alcohol and mix well into the batch. Add and mix sufficient purified water to provide 85 g of finished product.

Having now fully described this invention, it will be understood that the same can be practiced within a wide range of equivalent composition and administration values without affecting the scope or spirit of the invention or any embodiment thereof.

What is claimed as new and intended to be protected by Letters Patent of the United States is:

1. A method of treating androgen-related disorders in an animal which comprises administering to said animal dihydrotestosterone level decreasing amounts of a compound of formula (I):

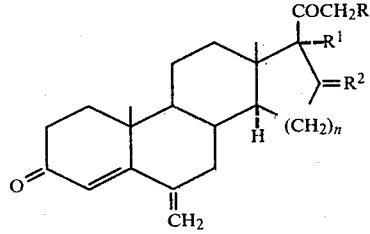

wherein $R = R^1 = H$, $R^2$ is $H_2$ and $n = 1$.

2. The method of claim 1 wherein the androgen-related disorder is selected from the group consisting of acne, seborrhea, and androgenic alopecia.

3. The method of claim 2 wherein the compound is administered as a topical preparation containing from 0.001% to 5% of the compound.

4. The method of claim 1 wherein the androgen-related disorder is selected from the group consisting of oily skin, hirsutism, benign prostatic hypertrophy and androgen dependent prostatic adenocarcinoma.

5. The method of claim 4 wherein said disorder is androgen dependent prostatic adenocarcinoma and the compound is administered together with a compound selected from the group consisting of megestrol acetate medrogestone and cyproterone acetate.

6. A pharmaceutical composition for topical application to the skin of a patient suffering from an androgen-related disorder which comprises 5α-dihydrotestosterone level decreasing amounts of a compound of the formula:

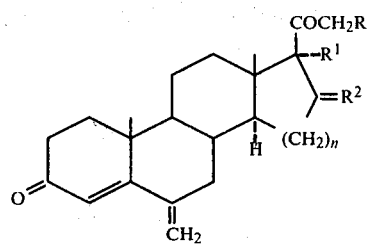

wherein $R = R^1 = H$, $R^2$ is $H_2$ and $n = 1$;
together with an inert topical pharmaceutical carrier.

7. The composition of claim 6 wherein said carrier is selected from oleaginous bases, silicones, lanolines, polyethylene glycol, glyceryl monostearate, methylcellulose and hydroxymethylcellulose.

8. The method of claim 4 wherein the compound is administered orally, by injection, by depot formulation, by implants or silastic implants in an amount of from 0.1 to 50 mg/kg.

* * * * *

UNITED STATES PATENT AND TRADEMARK OFFICE
CERTIFICATE OF CORRECTION

PATENT NO. : 4,396,615

DATED : August 2, 1983

INVENTOR(S) : Vladimir Petrow and Leon Lack

It is certified that error appears in the above-identified patent and that said Letters Patent is hereby corrected as shown below:

Column 1, line 35, delete "Ps".

Signed and Sealed this

Sixth Day of December 1983

[SEAL]

Attest:

Attesting Officer

GERALD J. MOSSINGHOFF

Commissioner of Patents and Trademarks